United States Patent [19]
Gorman

[11] Patent Number: 6,109,118
[45] Date of Patent: Aug. 29, 2000

[54] PARABOLIC PROPORTIONING LIQUID SAMPLER FOR FLUIDS IN HORIZONTAL TANKS TO ACCOMMODATE ACCURATE CHEMICAL ANALYSIS

[75] Inventor: Lee V. Gorman, Richardson, Tex.

[73] Assignee: Texas Instruments Incorporated, Dallas, Tex.

[21] Appl. No.: 08/218,540

[22] Filed: Mar. 28, 1994

[51] Int. Cl.[7] .................................................. G01N 1/00
[52] U.S. Cl. ................................... 73/864.63; 73/863.33; 73/863.81; 73/864.64
[58] Field of Search ........................... 73/863.33, 863.81, 73/863.82, 863.85, 864.63, 864.64, 864.67

[56] References Cited

U.S. PATENT DOCUMENTS

| | | | |
|---|---|---|---|
| 1,883,021 | 10/1932 | Silknitter | 73/864.64 |
| 3,024,660 | 3/1962 | Tothill | 73/864.64 |
| 4,072,059 | 2/1978 | Hamilton | 73/864.64 |
| 4,088,025 | 5/1978 | Foster et al. | 73/863.33 |
| 4,252,200 | 2/1981 | Peterson | 73/864.64 |
| 4,838,079 | 6/1989 | Harris | 73/863.33 |
| 4,854,182 | 8/1989 | Ryan et al. | 73/864.64 |
| 4,979,402 | 12/1990 | Ryan et al. | 73/864.64 |
| 5,179,859 | 1/1993 | Van Niekerk | 73/864.64 |
| 5,209,129 | 5/1993 | Jaselskis et al. | 73/864.64 |
| 5,237,878 | 8/1993 | Hackenberg | 73/863.33 |
| 5,341,693 | 8/1994 | Banu | 73/864.63 |

Primary Examiner—Eric S. McCall
Attorney, Agent, or Firm—W. Daniel Swayze, Jr.; W. James Brady, III; Frederick J. Telecky, Jr.

[57] ABSTRACT

A system and method of obtaining an accurate sample of a fluid in a container comprising providing a container for accommodating a fluid to be analyzed, providing a hollow vessel of predetermined varying internal volume dimensions from one end of the vessel to the opposing end of the vessel disposed within the container, permitting and then stopping fluid flow from the container into the vessel and removing fluid from the vessel for analysis. The axis of the hollow vessel is positioned vertically and the hollow vessel is provided with a plurality of vertically spaced apart apertures controlled by the valve for receiving the fluid. The predetermined varying internal fluid receiving volume dimensions are controlled by providing an insert in said vessel having volume dimensions inversely proportional to the volume dimensions of the container at each height level in the container. The container is preferably cylindrical and has rounded ends, the vessel is circular and the insert is of conical shape and has a varying diameter $D=d(h/r)[1-Z((3h^2+Z^2)/3r^2L)]$, where d is the inside diameter of the vessel, r is the radius of the cylinder, Z is the length of the rounded ends along the center line, h is the varying reference height from the container center line at which each incremental diameter D of the volume compensating insert exists and L is the length of the cylindrical portion of the container.

16 Claims, 2 Drawing Sheets

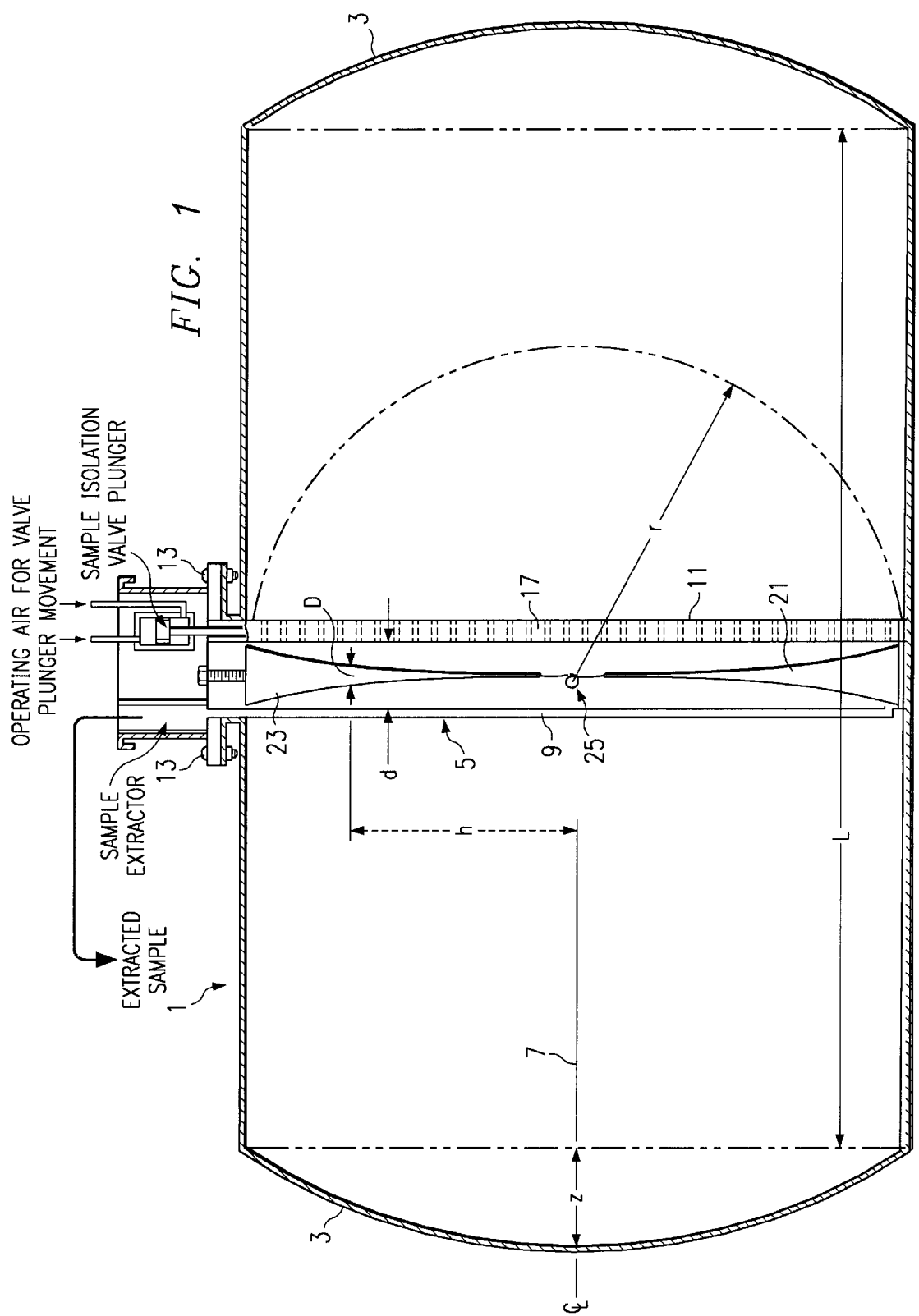

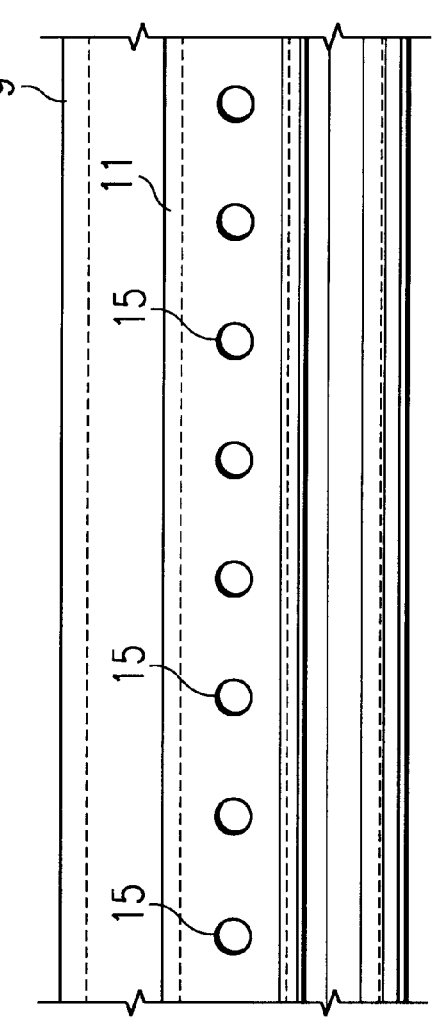
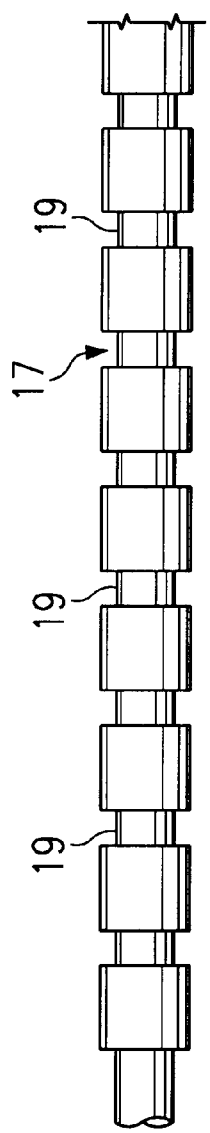
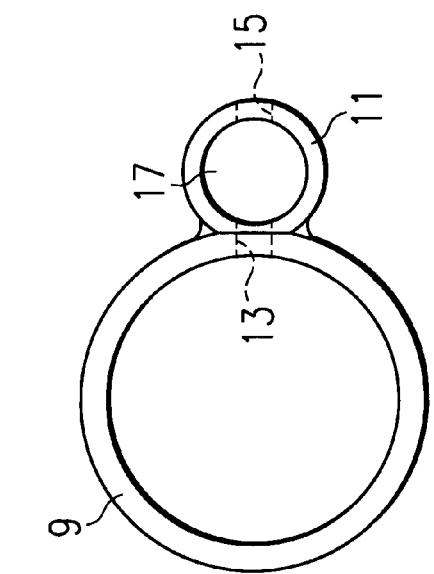

PARABOLIC PROPORTIONING LIQUID SAMPLER FOR FLUIDS IN HORIZONTAL TANKS TO ACCOMMODATE ACCURATE CHEMICAL ANALYSIS

BACKGROUND OF THE INVENTION

1. Field of the Invention

This invention relates to chemical analysis of fluids and, more specifically, to a method of obtaining a sample representative of the total contents of a container for analysis.

2. Brief Description of the Prior Art

Where solubility or miscibility is low, fluids, including both liquid and gases which can be either hazardous, non-hazardous or non-classified will ordinarily stratify into various thermal, density, composition and/or insoluble layers in a container. This is especially the case in bulk tanks where chemical mixtures are influenced by gravity as well as possibly for other reasons. Often, one chemical is not miscible with other chemicals such as, for example, a mixture of fuel oil, water and perchloroethylene. Such chemicals contained in the same tank would separate into three separate layers with the perchloroethylene on the bottom, water in the middle and the fuel oil on the top.

Often and almost always in the case of hazardous waste liquid materials that have stratified into layers, a representative sample of the non-homogeneous fluid is required for analysis and this analysis is intended to accurately represent the entire contents of the tank. Therefore, accuracy in extracting a proper sample to represent exactly the bulk liquid is critical and, to date, many means have been utilized to obtain a sample of such fluid for analysis. However, none of the prior art systems are capable of extracting a sample with the same composition proportions as the bulk liquid where stratification has occurred and this is especially true in the case of containers with non-uniform cross sections from top to bottom.

Prior art bulk liquid tank sampling techniques range from a valve in the bottom to drain off a sample into a jar, which only extracts off the bottom of the tank, to straight wall tubes dipped into the tank which extend from the top of the tank to the bottom thereof. In the latter case the tube bottom is open and the liquid enters the tube bottom on the way down and then the tube bottom is closed before the tube is withdrawn and the sample extracted. This latter method provides a reasonably accurate sample if the tank has straight flat vertical parallel walls or, in other words, uniform cross-section from top to bottom. However, this latter system generally is incapable of meeting the accuracy requirements for round horizontal tanks or other tanks that do not contain the same cross-sectional volume for each increment of variation in liquid height from center to top and center to bottom. Other prior art techniques involve extraction of a fixed amount (such as one cubic centimeter) of sample on a time interval basis from the output pipe as the bulk liquid is withdrawn. This method is very popular, however it involves numerous errors and variables and is not acceptable as an accurate, reliable procedure. The bulk extraction rate from the tank in not proportioned to the rate of change in volume of the tank (including all the various layers) as the tank is emptied for removal and disposal. No known attempts have been made to consider the radial effects of a tank on the sample quality and no available equipment is known to exist at present that proportions sample extraction with the corresponding bulk liquid tank volume to correct for the radial changes in the vertical walls of the tank.

SUMMARY OF THE INVENTION

In accordance with the present invention, the above described problems of the prior art are minimized and there is provided a system which takes into account the shape of the tank containing the fluids to be examined.

Briefly, the volume changes in horizontal round bulk liquid tanks are taken into account for sample extraction where the fluid mixtures within the tank have been stratified to represent the bulk composition based upon the sampler designs that compensate for the radial changes and non-linearity of the volume for each increment of the tank height.

The liquid in all bulk tanks is not single component, pure, and/or miscible in all proportions to allow for sampling accuracy when a representative amount is required for analysis or assessment. Such situations of non-linearity exist most often in round or circular bulk tanks that are horizontal and recognition has been made that a true representative sample of such liquids that have stratified into thermal, density and/or composition layers of varying degrees is a function of the curvature of the tank wall—a mirror image concept along the vertical center of gravity. Also, the curvature of the tank ends is involved in this volumetric relation unless the ends are flat with essentially no curvature. The sampling device extends the full diameter of the tank, top-to-bottom, with allowances to accommodate for materials of construction (internal diameter is measured). The entire sampling device is port or flange adapted into the top of the tank for ease of operation, removal, inspection and maintenance.

Many concepts are valid design styles for such a sampler, however the one that is considered as the most practical and reliable is a fixed mechanical cavity whereby a full-diameter length hollow tube is fitted with identical parabolic cones such that the cone points face each other at the tank center (inside the hollow straight-wall tube). In the design for these parabolic cones, the cone points may be rounded off at the position up from the cone base where the cone diameter becomes less than some predetermined amount, such as, for example, ¼ inch.

The next aspect in such a design is to obtain a representative sample of the bulk liquid within the sample cavity along the entire vertical length dimension to allow the liquid in both the sample tube and bulk tank to stay in level composition contact through direct access in the tube wall. The sample will be representative of the bulk liquid within the bulk tank in view of the dimensioning of the conical elements disposed within the sample cavity as will be explained in detail hereinbelow. The sample is then extracted from the sample cavity and analyzed in standard manner.

BRIEF DESCRIPTION OF THE DRAWINGS

FIG. 1 is a cross-sectional view of a parabolic sampler for horizontal liquid bulk tanks in accordance with the present invention;

FIG. 2 is a top view of the sample extractor assembly in accordance with the present invention;

FIG. 3 is a side view of the sample extractor assembly in accordance with the present invention; and FIG. 4 is a side view of a plunger in accordance with the present invention.

DESCRIPTION OF THE PREFERRED EMBODIMENT

Referring to FIG. 1, there is shown the sampler concept in accordance with the present invention with the dimensional variables. The liquid bulk tank 1 is cylindrical in shape with cylinder cross-section radius r and cylinder length L, the tank having rounded end sections 3 having a dimension Z along the center line 7 of the cylindrical portion from the end of the cylindrical portion of the tank to the internal end of the rounded end section.

Within the tank 1 and extending normal to the center line 7 of the cylindrical portion of the tank is a sample extractor 5 which will be described in detail hereinbelow. The sample extractor 5 extends between the topmost and bottommost portions of the cylindrical portion of the tank 1 and normal to the center line 7 so that it spans all strata of fluid contained therein. The sample extractor 5 can be removable from the tank so that a sample can be entered therein and the extractor then removed from the tank or the sample extractor can be permanently affixed within the tank with the sample being entered into and extracted from the sample extractor in situ after closing the apertures between the extractor and the tank. As shown in FIG. 1, the sample extractor 5 is removable from the tank 1 by removal of securing agents 13 shown as screws which secure the sample extractor 5 in position as shown within the tank.

Referring now to the sample extractor 5, it includes a pair of circular tubes 9 and 11 as shown in FIGS. 1 and 2, there being a plurality of apertures 13 spaced apart vertically a predetermined distance and interconnecting the tubes 9 and 11. The spacing between apertures 13 has been chosen to be 1 inch in the preferred embodiment, however there is nothing critical about this distance, it being understood that the closer together the apertures, the more accurately will the sample replicate the contents of the tank. The tube 11 includes a second set of apertures 15 therein as best shown in FIGS. 2 and 3, preferably but not necessarily at the same heights as the apertures 13 and spaced from the apertures 13 around the circumference of the tube 11, the only requirement of apertures 15 being that they be selectively communicable with the apertures 13 so that fluid can travel from the tank 1 into the tube 9 via apertures 13 and 15 and tube 11. A plunger 17, best shown in FIG. 4, is disposed for vertical movement within the tube 11. The plunger 17 provides a slip-seal fit within the tube 11 so that fluid cannot travel vertically therealong. The plunger 17 has a plurality of grooves 19 which are spaced apart the same distance as the apertures 13 and 15 and sufficiently long to extend from an aperture 13 to an aperture 15 so that fluid can travel from an aperture 15 to an aperture 13 via a groove 19 when a groove is aligned with both an aperture 13 and an aperture 15 and so that fluid cannot travel between these apertures when the groove 19 is not so aligned. The sample extractor 5 includes some standard mechanism for causing vertical travel of the plunger 17, this being shown in FIG. 1.

Referring now to the tube 9, in order to insure that the amount of sample collected at each level within the tank is representative of the volume of the tank at that level, the available volume at each level within the tube 9 must be altered to accommodate the actual volumes at these levels within the tank 1. This is accomplished by providing a pair of conical elements with parabolically shaped surfaces 21 and 23 within the tube 9 as shown in FIG. 1. The conical element 21 rests at the bottom of the tube 9 on its flat surface whereas the conical element 23 rests in the tube 9 above the element 21 but inverted so that the apices of the elements 21 and 23 are adjacent each other. The base of the conical element 23 is disposed at the height of the top inner surface of the tank 1, the elements 21 and 23 being coupled together at their apices by a cable 25 or the like to enable easy removal of the lower conical element 23 for cleaning or the like. Each conical element has a diameter D that varies according to the equations set forth hereinbelow as the distance h from the container center line 7 varies from 0 to h=r, the radius of the cross section of the cylindrical portion of the tank 1. The distance h is the varying reference height from the container center line 7 at which each incremental diameter D of the volume compensating inserts 21 and 23 exist. The tube 9 has an inside fixed diameter d. The variation in the diameter of the conical elements is designed to present an available volume at each aperture 13 level in the tube 9 proportional to the volume of the tank 1 at that tank level.

The conical elements 21 and 23 are shaped in accordance with the shape of the tank 1 according to the following equations:

The equation $D=d(h/r)=(h)d/r$ represents the diameter of the cone at various levels and provides the change in the parabolic cone diameter for a tank with flat ends as the sample chamber volume varies with liquid height from the bottom of the tank to the center and then vertically to the top of the tank (a mirror image). It follows that the distance $h=Dr/d=D(r/d)$. The equation $D=d(h/r)[1-Z(3h^2+Z^2)/3r^2L]$ relates the change of the cone diameter for a tank with rounded ends. The equation $V=\pi d^2 r/693$ (for flat end tanks) or $V=\pi d^2 r/656$ (for rounded end tanks less than 10,000 gallons), where V is the volume of the sample in gallons, is a simplified way to closely estimate the inside diameter of the hollow tube section such that a given (or predetermined) volume of sample is collected for a full tank. This calculation is critical since the mechanical aspects of the design depend upon the hollow tube inside diameter and this fixes the finished device volume. All length dimensions in the above equations are in inches.

In operation, the sample extractor 5 is properly positioned within the container 1 with the properly dimensioned conical elements 21 and 23 in place and the plunger 17 is moved in the tube 11 until the groove 19 is aligned with the apertures 13 and 15 so that fluid at each aperture level in the container 1 will travel into the tube 9 and fill the tube 9. At this time, an accurate sample of the contents of the container 1 should be disposed within the tube 9. The plunger 17 is then moved again in the tube 11 until the grooves 19 are out of communication with the apertures 13 and 15 and the sample extractor 5 is then removed from the container 1 and the sample is withdrawn for analysis.

Referring to FIGS. 2 to 4, the design of the sampler isolation valve and valve plunger assembly requires that the valve body cylinder be flattened on one side as well as the sampler tube cylinder to allow for welding together along both edges of the mated (flattened) sides. Once this is completed, holes may be bored through the valve body cylinder tube and the welded tubes. Thereafter, both the sampler tube inside diameter and the valve body cylinder are reamed to remove burrs and to finish the valve body cylinder inside diameter to "slip-seal" with the valve plunder outside diameter.

Sample extraction is accomplished in any number of ways such as by a tube plumbed into the sampler tube cylinder at the bottom and either removed using air pressure on the cylinder to force the sample out and into a container for analysis or by directly removing the sample with a positive displacement pump. The valve plunger is operated by an air piston cylinder either up or down to open or close the bulk fluid to sampler access holes.

Materials of construction are selected to resist the chemical environment in the bulk liquid tank and to be compatible in characteristics to accomplish the designs and operational functions.

Though the invention has been described with respect to a specific preferred embodiment thereof, many variations and modifications will immediately become apparent to those skilled in the art. It is therefore the intention that the appended claims be interpreted as broadly as possible in view of the prior art to include all such variations and modification.

What is claimed is:

1. A system for obtaining an accurate sample of a fluid, comprising:
   a container having a longitudinal axis for accommodating the fluid to be analyzed;
   a hollow vessel of predetermined varying internal fluid receiving volume dimensions from one end of said vessel to an opposing end of said vessel disposed within said container; and
   means to permit and stop fluid flow from said container into said vessel in at least three positions substantially along the longitudinal axis.

2. The system of claim 1 wherein the longitudinal axis of said hollow vessel is positioned vertically.

3. The system of claim 1 wherein said hollow vessel includes a plurality of vertically spaced apart apertures controlled by said valve for receiving a fluid.

4. The system of claim 2 wherein said hollow vessel includes a plurality of vertically spaced apart apertures controlled by said valve for receiving a fluid.

5. The system of claim 1 wherein said predetermined varying internal fluid receiving volume dimensions are controlled by an insert in said vessel having volume dimensions inversely proportional to the volume dimensions of said container at each height level in said container.

6. The system of claim 4 wherein said predetermined varying internal fluid receiving volume dimensions are controlled by an insert in said vessel having volume dimensions inversely proportional to the volume dimensions of said container at each height level in said container.

7. A system for obtaining an accurate sample of a fluid, comprising:
   a container having a longitudinal axis for accommodating the fluid to be analyzed;
   a hollow vessel of predetermined varying internal fluid receiving volume dimensions from one end of said vessel to an opposing end of said vessel disposed within said container; and
   means to permit and stop fluid flow from said container into said vessel in at least three positions substantially alone the longitudinal axis, wherein said predetermined varying internal fluid receiving volume dimensions are controlled by an insert in said vessel having volume dimensions inversely proportional to the volume dimensions of said container at each height level in said container, and wherein said container has a cylindrical section and has rounded ends, said vessel is circular in cross section and said insert is of conical shape and has a varying diameter $D=d(h/r)[1-Z((3h^2+Z^2)/3r^2L)]$, where d is the inside diameter of said vessel, h is the height corresponding to D in said vessel in a direction normal to a center line of said container, r is the radius of said cylindrical section, Z is the length of said rounded ends along said center line and L is the length of the cylindrical section of said container.

8. A system for obtaining an accurate sample of a fluid, comprising:
   a container having a longitudinal axis for accommodating the fluid to be analyzed;
   a hollow vessel of predetermined varying internal fluid receiving volume dimensions from one end of said vessel to an opposing end of said vessel disposed within said container; and
   means to permit and stop fluid flow from said container into said vessel in at least three positions substantially along the longitudinal axis, wherein the axis longitudinal of said hollow vessel is positioned vertically, wherein said predetermined varying internal fluid receiving volume dimensions are controlled by an insert in said vessel having volume dimensions inversely proportional to the volume dimensions of said container at each height level in said container, and wherein said container has a cylindrical section and has rounded ends, said vessel is circular in cross section and said insert is of conical shape and has a varying diameter $D=d(h/r)[1-Z((3h^2+Z^2)/3r^2L)]$, where d is the inside diameter of said vessel, h is the height corresponding to D in said vessel in a direction normal to a center line of said container, r is the radius of said cylindrical section, Z is the length of said rounded ends along said center line and L is the length of the cylindrical section of said container.

9. A method of obtaining an accurate sample of a fluid in a container comprising the steps of:
   forming a container for accommodating a fluid to be analyzed with a longitudinal axis;
   varying predetermined internal volume dimensions of a hollow vessel from one end of said vessel to an opposing end of said vessel disposed within said container;
   starting and stopping fluid flow from said container into said vessel in a least three positions substantially along the longitudinal axis; and
   removing said fluid from said vessel for analysis.

10. The method of claim 9 wherein the longitudinal axis of said hollow vessel is positioned vertically.

11. The method of claim 9 wherein said hollow vessel is formed with a plurality of vertically spaced apart apertures controlled by a valve for receiving said fluid.

12. The method of claim 10 wherein said hollow vessel is formed with a plurality of vertically spaced apart apertures controlled by a valve for receiving said fluid.

13. The method of claim 9 further including controlling said predetermined varying internal fluid receiving volume dimensions by providing an insert in said vessel having volume dimensions inversely proportional to the volume dimensions of said container at each height level in said container.

14. The method of claim 10 further controlling said predetermined varying internal fluid receiving volume dimensions by providing an insert in said vessel having volume dimensions inversely proportional to the volume dimensions of said container at each height level in said container.

15. A method of obtaining an accurate sample of a fluid in a container comprising the steps of:
   forming a container for accommodating a fluid to be analyzed with a longitudinal axis;
   varying predetermined internal volume dimensions of a hollow vessel from one end of said vessel to an opposing end of said vessel disposed within said container;
   starting and stopping fluid flow from said container into said vessel in a least three positions substantially alone the longitudinal axis; and removing said fluid from said vessel for analysis, controlling said predetermined varying internal fluid receiving volume dimensions by providing an insert in said vessel having volume dimensions inversely proportional to the volume dimensions of said container at each height level in said container, wherein said container has a cylindrical section and has rounded ends, said vessel is circular in cross section and said insert is of conical shape and has a varying diameter $D=d(h/r)[1-Z((3h^2+Z^2)/3r^2L)]$, where d is the inside diameter of said vessel, h is the height corresponding to D in said vessel in a direction normal to a center line of said container, r is the radius of said cylindrical section, Z is the length of said rounded ends along said center line and L is the length of the cylindrical section of said container.

16. A method of obtaining an accurate sample of a fluid in a container comprising the steps of:

forming a container for accommodating a fluid to be analyzed with a longitudinal axis;

varying predetermined internal volume dimensions of a hollow vessel from one end of said vessel to an opposing end of said vessel disposed within said container;

starting and stopping fluid flow from said container into said vessel in a least three positions substantially along the longitudinal axis; and removing said fluid from said vessel for analysis;

wherein the longitudinal axis of said hollow vessel is positioned vertically;

controlling said predetermined varying internal fluid receiving volume dimensions by providing an insert in said vessel having volume dimensions inversely proportional to the volume dimensions of said container at each height level in said container;

wherein said container has a cylindrical section and has rounded ends, said vessel is circular in cross section and said insert is of conical shape and has a varying diameter $D=d(h/r)[1-Z((3h^2+Z^2)/3r^2L)]$, where d is the inside diameter of said vessel, h is the height corresponding to D in said vessel in a direction normal to a center line of said container, r is the radius of said cylindrical section, Z is the length of said rounded ends along said center line and L is the length of the cylindrical section of said container.

* * * * *